US008257624B2

(12) United States Patent
Favis et al.

(10) Patent No.: US 8,257,624 B2
(45) Date of Patent: Sep. 4, 2012

(54) POROUS NANOSHEATH NETWORKS, METHOD OF MAKING AND USES THEREOF

(76) Inventors: Basil D. Favis, Kirkland (CA); Pierre Sarazin, Montreal (CA); Xavier Roy, St-Michel des Saints (CA)

( * ) Notice: Subject to any disclaimer, the term of this patent is extended or adjusted under 35 U.S.C. 154(b) by 402 days.

(21) Appl. No.: 12/093,712

(22) PCT Filed: Nov. 14, 2006

(86) PCT No.: PCT/CA2006/001852
§ 371 (c)(1),
(2), (4) Date: Oct. 20, 2008

(87) PCT Pub. No.: WO2007/053955
PCT Pub. Date: May 18, 2007

(65) Prior Publication Data
US 2009/0087641 A1 Apr. 2, 2009

Related U.S. Application Data

(60) Provisional application No. 60/735,890, filed on Nov. 14, 2005.

(51) Int. Cl.
*B29C 67/20* (2006.01)
(52) U.S. Cl. .......... 264/49; 264/413; 264/414; 264/415; 264/36.11; 264/41; 264/42; 264/44; 264/45.1; 264/45.9; 264/48; 264/651; 264/637; 264/510; 264/514; 264/288.8; 264/916
(58) Field of Classification Search .................. 264/413, 264/48, 637, 651, 49, 41, 42, 45.1, 319, 414, 264/415, 36.11, 44, 45.9, 510, 514, 288.8, 264/916; 106/672
See application file for complete search history.

(56) References Cited

U.S. PATENT DOCUMENTS 5,856,367 A * 1/1999 Barrows et al. ................. 521/64
(Continued)

FOREIGN PATENT DOCUMENTS

CA 2 512 072 7/2007
(Continued)

OTHER PUBLICATIONS

Caruso et al. "Characterization of Polyelectrolyte-Protein Multilayer Films by Atomic Force Microscopy, Scanning Electron Microscopy, and Fourier Transform Infrared Reflection-Absorption Spectroscopy." *Langmuier*. vol. 14. 1998. pp. 4559-4565.

(Continued)

*Primary Examiner* — Jeff Wollschlager
*Assistant Examiner* — Stella Yi
(74) *Attorney, Agent, or Firm* — Goudreau Gage Dubuc; Alain M. Leclerc

(57) ABSTRACT

A method for making a porous material, includes melt-blending two or more non-miscible polymers to obtain a co-continuous melt, solidifying the melt to obtain a solid mass consisting of two co-continuous polymer phases, and selectively extracting one of the co-continuous phases thereby creating within the solid mass an essentially continuous pore network having an internal surface. The method further includes replicating the internal surface of the pore network within the solid mass by coating the internal surface with successive layers of materials, and selectively extracting the solid mass without extracting the layers of materials, to thereby yield the product porous material, formed of the layers of materials. The material has a void fraction higher than about 75%, and mainly having essentially fully interconnected sheath-like non-spherical pores and essentially non-fibrous walls.

16 Claims, 7 Drawing Sheets

U.S. PATENT DOCUMENTS 6,673,285 B2     1/2004    Ma
6,929,764 B2     8/2005    Jiang et al.

FOREIGN PATENT DOCUMENTS

WO     WO 2006/059984     6/2006

OTHER PUBLICATIONS

Caruso et al. "Nanoengineering of Inorganic and Hybride Hollow Spheres by Colloidal Templating." *Science*. vol. 282. No. 5391. 1998. pp. 1111-1114.

Caruso et al. "Protein Multilayer Formation on Colloids through a Stepwise Self-Assembly Technique." *J. Am. Chem. Soc.* vol. 121. 1999. pp. 6039-6046.

Decher et al. "Buildup of ultrathin multilayer films by a self-assembly process:III. Consecutively alternating adsorption of anionic and cationic polyelectrolytes on charged surfaces." *Thin Solid Films*. vol. 210. 1992. pp. 831-835.

Decher et al. "Fuzzy Nanoassemblies: Toward Layered Polymeric Multicomposites." *Science*. vol. 277. 1997. pp. 1232-1237.

Donath et al. "Novel Hollow Polymer Shells by Colloid-Templated Assembly of Polyelectrolytes." *Angew. Chem. Int. Ed.* vol. 37. No. 16. 1998. pp. 2201-2205.

Dubas et al. "Factors Controlling the Growth of Polyelectrolyte Multilayers." *Macromolecules*. vol. 82. 1999. pp. 8153-8160.

Harris et al. "Open pore biodegradable matrices formed with gas foaming." 1998. pp. 396-402.

Kim et al. "Molecular Packing of Lysozyme, Fibrinogen, and Bovine Serum Albumin on Hydrophilic and Hydrophobic Surfaces Studied by Infrared-Visible Sum Frequency Generation and Fluorescence Microscopy." *J. Am. Chem. Sco.* vol. 125. 2003. pp. 3150-3158.

Kotov. "Layer-by-Layer Self Assembly: The Contribution of Hydrophobic Interactions." *Nanostructured Materials*. vol. 12. 1999. pp. 789-796.

Liu et al. "Surface Engineering of Nano-Fibrous Poly (L-Lactic Acid Scaffolds via Self-Assembly Technique for Bone Tissue Engineering." *J. of Biomedical Nanotechnology*. vol. 1. 2005. pp. 54-60.

Lvov et al. "Assembly of Multicomponent Protein Films by Means of Electrostatic Layer-by-Layer Adsorption." *J Am. Chem. Soc.* vol. 117. 1995. pp. 6117-6123.

Mikos et al. "Preparation and characterization of poly(L-lactic acid) foams." *Polymer*. vol. 35. No. 5. 1994. pp. 1068-1077.

Mikos et a. "Preparation of poly(glycolic acid) bonded fiber structures for cell attachment and transplantation." *J. of Biomedical Materials Research*. vol. 27. 1993. pp. 183-189.

Poptoshev et al. "Influence of Solvent Quality on the Growth of Polyelectrolyte Multilayers." *Langmuir*. vol. 20. 2004. pp. 829-834.

Roy et al. "Ultraporous Nanosheath Materials by Layer-by-Layer Deposition onto Co-continuous Polymer-Blend Templates." *Advanced Materials*. vol. 18. 2006. pp. 1015-1019.

Sarazin et al. "Controlled preparation and properties of porous poly(L-lactide) obtained from a co-continuous blend of two biodegradable polymers." *Biomaterials*. vol. 25. 2004. pp. 5965-5978.

Sarazin et al. "Morphology Control in Co-continuous Poly(L-lactide)/Polystryrene Blends: A Route towards highly structured and Interconnected Porosity in Poly(L-lactide) Materials." *Biomacromolecues*. vol. 4. 2003. pp. 1669-1679.

Schlenoff et al. "Mechanism of Polyelectrolyte Multilayer Growth: Charge Overcompensation and Distribution. "*Macromolecules*. vol. 34. 2001. pp. 592-598.

Schoeler et al. "Investigation of the Influence of Polyelectrolyte Charge Density on the Growth of Multilayer Thin Films Prepareed by the Layer-by-Layer Technique." *Macromolecules*. vol. 35. 2002. pp. 889-897.

Schugens et al. "Biodegradable and macroporous polylactide implants for cell transplantation: I. Preparation of macroporous polylactide supports by solid-liquid phase separation." *Polymer*. vol. 37. No. 6. 1996. pp. 10-27-1038.

Schugens et al. "Polylactide macroporous biodegradable implants for cell transplantation:II. Preparation of polylactide forams by liquid-liquid phase separation." *J. of Biomedical Materials Research*. vol. 30. 1996. pp. 449-461.

Segura et al. "Crosslinked hyaluronic acid hydrogels: a strategy to functionalize and pattern." *Biomaterials*. vol. 26. 2005. pp. 359-371.

Virgilio et al. "High Contrast Imaging of Interphases in Ternary Polymer Blends Using Focused Ion Beam Preparation and Atomic Force Microscopy." *Macromolecules*.

Yuan et al. "Coarsening of Immiscible Co-Continuous Blends During Quiescent Annealing." *AIChE Journal*. vol. 51. No. 1. 2005. pp. 271-280.

Yuan et al. "Macroporous ploy(L-lactide) of controlled pore size derived from the annealing of co-continuous polystyrene/poly(L-lactide) blends." *Biomaterials*. vol. 25. 2004. pp. 2161-2170.

\* cited by examiner

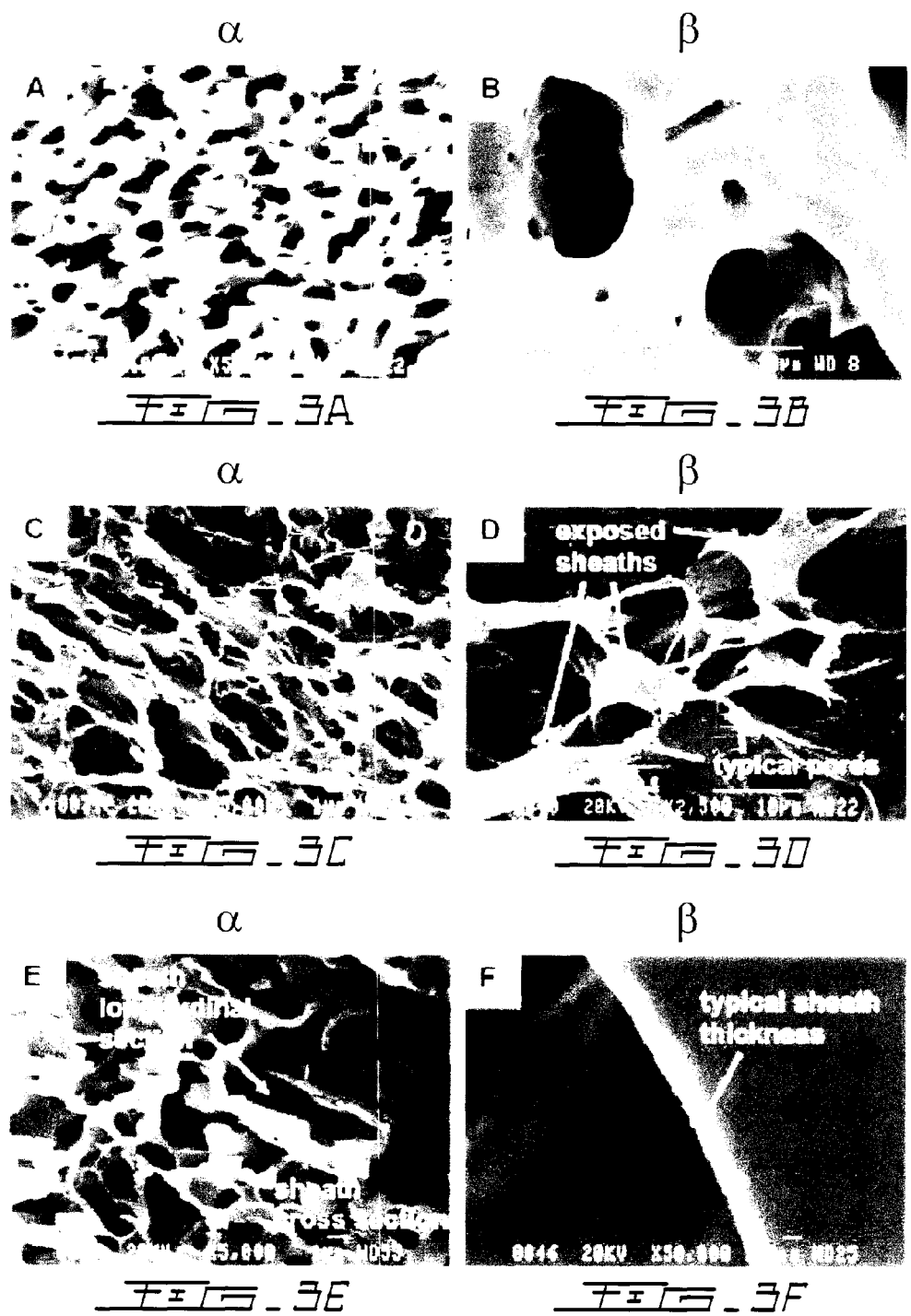

| Stage | A-PLLA/PCL 50/50 blend | |
|---|---|---|
| Series | α | β |
| Average pore diameter $d_\eta$ (μm) | – | – |
| % of the initial weight | 100 | 100 |
| Porosity (%) | 0 | 0 |
| Internal surface area per unit volume (μm$^{-1}$) | 0 | 0 |

| Stage | B-Porous PLLA template | |
|---|---|---|
| Series | α | β |
| Average pore diameter $d_n$ (μm) | 1.4 | 6.3 |
| % of the initial weight | 55.5 | 56.5 |
| Porosity (%) | 47.1 | 46.1 |
| Internal surface area per unit volume (μm$^{-1}$) | 1.3 | 0.29 |

| Stage | C-Polymer/protein multilayers assembled PLLA template | |
|---|---|---|
| Series | α | β |
| Average pore diameter $d_\eta$ (μm) | 1.4 | 6.3 |
| % of the initial weight | 56.6 | 56.8 |
| Porosity (%) | 46.1 | 45.8 |
| Volume variation after freeze-drying (%) | — | — |
| Internal surface area per unit volume (μm$^{-1}$) | 1.2 | 0.27 |
| Internal surface area per unit volume corrected for volume variation (μm$^{-1}$) | — | — |
| Specific surface area (m$^2$g$^{-1}$) | — | — |

| Stage | D-Composite polymer/protein ultra-porous structure | |
|---|---|---|
| Series | α | β |
| Average pore diameter $d_n$ (μm) | 1.8 | 6.4 |
| % of the initial weight | 1.5 | 0.3 |
| Porosity (%) | 98.7 | 99.6 |
| Volume variation after freeze-drying (%) | +10 | −25 |
| Internal surface area per unit volume (μm$^{-1}$) | 2.3 | 0.63 |
| Internal surface area per unit volume corrected for volume variation (μm$^{-1}$) | 2.5 | 0.47 |
| Specific surface area (m$^2$g$^{-1}$) | 140 | 63 |

POROUS NANOSHEATH NETWORKS, METHOD OF MAKING AND USES THEREOF

CROSS-REFERENCE TO RELATED APPLICATIONS

This application is a National Entry Application of PCT application No. PCT/CA2006/001852 filed on Nov. 14, 2006 and published in English under PCT Article 21(2), which itself claims the benefit of U.S. provisional application No. 60/735,890, filed on Nov. 14, 2005. All documents above are incorporated herein in their entirety by reference.

FIELD OF THE INVENTION

The present invention relates to the field of porous materials.

BACKGROUND OF THE INVENTION

Porous polymeric materials with interconnected porosity are receiving great attention recently due to their wide range of potential applications. These potential applications touch various fields such as: biomedical and pharmaceutical applications [tissue engineering, extra-corporeal devices such as those that are connected to the body to assist in surgery or dialysis, implantable medical devices that serve for example as substitutes for blood vessels, intra-ocular lenses, bio-sensing electrodes, catheters, and drug and gene delivery (for example as substrate for controlled release)], materials for chromatographic and other separation techniques (such as filtration, dialysis and osmosis), materials for diagnostic devices such as lateral flow devices, flow through devices and other immunoassay devices, catalysis of chemical and biochemical reactions, materials for conductivity applications and the list goes on.

In the sphere of tissue engineering, porous materials have particular use as polymeric scaffolding for cell tissue engineering. Interconnectivity of the pore network is essential for tissue ingrowth, vascularization and diffusion of nutrients. Controlled pore size distribution and large void volumes are other important features.

Much scientific effort is focused on biodegrable polymers such as poly(alpha esters) such as poly(lactic acid), poly (glycolic acid) and their copolymers. Such materials are approved for human clinical use in many jurisdictions.

Five different techniques to fabricate interconnected porous polymeric substrates for tissue engineering applications have been developed: textile process (ref 1), particulate leaching (ref 2), gas foaming (ref 3), thermally induced phase separation (refs 4 and 5) and hydrogel cross-linking (ref 6). However, every one of these approaches suffers from severe limitations including: low levels of interconnectivity; low void volume; structural fragility; difficulties in functionalization; poor control of pore size and distribution; and difficulties in obtaining reproducible porosities and large 3D articles.

Recently, an approach to preparing microporous materials, based on the melt-blending of two immiscible polymers, has been described (refs 7-10). It was shown that selective extraction of one of two components in a co-continuous structure can result in a single component structure of fully interconnected porosity with finely controlled pore size, porosity and morphology. This technique can generate porosities with high surface areas and pore diameters ranging from as low as about 100 nanometers upwards to hundreds of microns (refs 8-10). On the other hand this approach is limited in the void volume that can be attained and it can be used to prepare only relatively low void volume substrates (75%).

In an entirely different field of scientific activity, self-assembly via layer-by-layer (LBL) deposition is gaining significant attention. LBL deposition is a simple and effective approach to deposit ultrathin and uniformly assembled molecular layers on surfaces (refs 11 and 12). In that approach, polyelectrolytes are adsorbed on an oppositely charged surface, reversing the surface charge and leaving it primed for the next deposition cycle (refs 13 and 14). The resulting structure is multilayered with each molecular layer composed of oppositely charged polyelectrolytes. The thickness of each layer can be closely controlled through the salinity of the polyelectrolyte solution (refs 13 and 14), the quality of the solvent (ref 15) and the charge density on the polyion chain (ref 16). Deposition time, polyelectrolyte concentration and molecular weight are known to be less important parameters (ref 12). Originally exclusively investigated on macroscopically flat surfaces, this technique has been recently used to fabricate hollow spheres by assembling multilayered films onto colloidal particles and subsequently removing the core (refs 17 and 18).

To date, however, no work has been reported on the use of LBL techniques to create 3-dimensional, fully interconnected substrates.

SUMMARY OF THE INVENTION

The present invention provides a method for making a porous material and the material produced thereof. This method comprising the steps of:
  (a) melt-blending two or more non-miscible polymers, for example poly(L-lactic acid) and poly($\epsilon$-caprolactone), to obtain a co-continuous melt;
  (b) solidifying the melt of step (a) to obtain a solid mass;
  (c) selectively extracting at least one of the polymers from the solid mass, thereby creating an essentially continuous pore network within the solid mass, said pore network having an internal surface;
  (d) replicating the internal surface of the pore network within the solid mass by coating said internal surface with successive layers; and
  (e) selectively extracting the solid mass without extracting the layers, thereby producing a porous material, this extraction being complete or partial depending on the desired mechanical properties of the resulting material;

In this method, the alternating layers can optionally be polymeric layers. Also, this method can optionally further comprise, after step (b), a quiescent annealing of the solid mass obtained. It can also further comprise, after step (c), the step of depositing one or more precursor layers on the internal surface of said pore network. This method can also further comprise, after step (e), the step of exchanging the solvent and freeze-drying the porous material.

The present invention also provides novel porous materials having a void fraction higher than about 75% and mainly consisting of essentially fully interconnected sheath-like non-spherical pores and essentially non-fibrous walls. Preferably, these materials will have a void fraction higher than 90%. More preferably, these materials will have a void fraction ranging from 98.7% to 99.6%. Preferably, these materials will exhibit average pore wall thickness of about 100 nanometers, a specific surface area of about 0.4 to about 140 m$^2$/gram or an internal surface area per unit volume of about 0.29 to about 2.3 $\mu m^{-1}$ for pore diameters ranging from 1.8 to 6.4 $\mu m$.

This invention also relates to the use of the porous materials of the present invention in tissue engineering, as a substrate for controlled release applications and as an implantable medical device.

Herein, the term "polymer" is meant to refer to naturally occurring or synthetic organic compounds of relatively high molecular weight comprising several linked units. Examples of polymers are, without being so limited, poly(diallyldimethylammonium chloride), poly(sodium 4-styrenesulfonate), poly(L-lactic acid), poly(ε-caprolactone), bovine serum albumin, and proteins.

Herein, the terms "layers" and "polymeric layers" are meant to refer to layers of molecules that, in the case of polymeric layers, comprise at least one polymer. These layers can comprise a variety of small molecules as well as macromolecular assemblies to such as cells. Notably, these layers can comprise, without being so limited, synthetic polymers, polyelectrolytes proteins, cell growth promoters, and functionalizing agents.

Herein, the term "functionalizing agent" is meant to refer to an agent that can provide some chemical functionality.

Other objects, advantages and features of the present invention will become more apparent to a person skilled in the art to which they pertain upon reading of the following non-restrictive description of specific embodiments thereof, given by way of example only with reference to the accompanying drawings.

DESCRIPTION OF THE DRAWINGS

FIG. 3 depicts scanning electron micrographs of microstructures of series α (A, C, E) and β (B, D, F). Micrographs (A) and (B) represent the morphologies of the porous structures obtained after melt-blending and extraction of the PCL porogen phase (Stage B, FIG. 1); Photos (C) and (D) are taken after LBL deposition onto the PLLA porous template and extraction of the PLLA phase (Stage D, FIG. 1); photo (E) is taken after LBL deposition and partial extraction of the PLLA; and photo (F) shows a typical sheath thickness of about 100 nm in the final porous structure (β) after deposition of 4 PDADMAC/BSA bilayers. The porous structures were prepared using a focused ion beam (FIB) apparatus (ref 19) to minimize macroscopic deformation or collapse of the structure;

DESCRIPTION OF ILLUSTRATIVE EMBODIMENTS

The present invention provides new porous materials and a method for making these high void volume materials. The method comprises LBL deposition on a porous co-continuous blend template followed by selective extraction of the template.

A clear advantage of the present method of prior art advances is the capability of close control over a wide range of pore size and void volume (up to 99.6%), combined with an interconnectivity of the pores network of 100%. Also, the use of the LBL deposition approach allows for an easy and straightforward functionalization of the structure by incorporating into the process bio- or chemically-active molecules, conducting polymers, functionalizing agents, etc.

Figure 1:
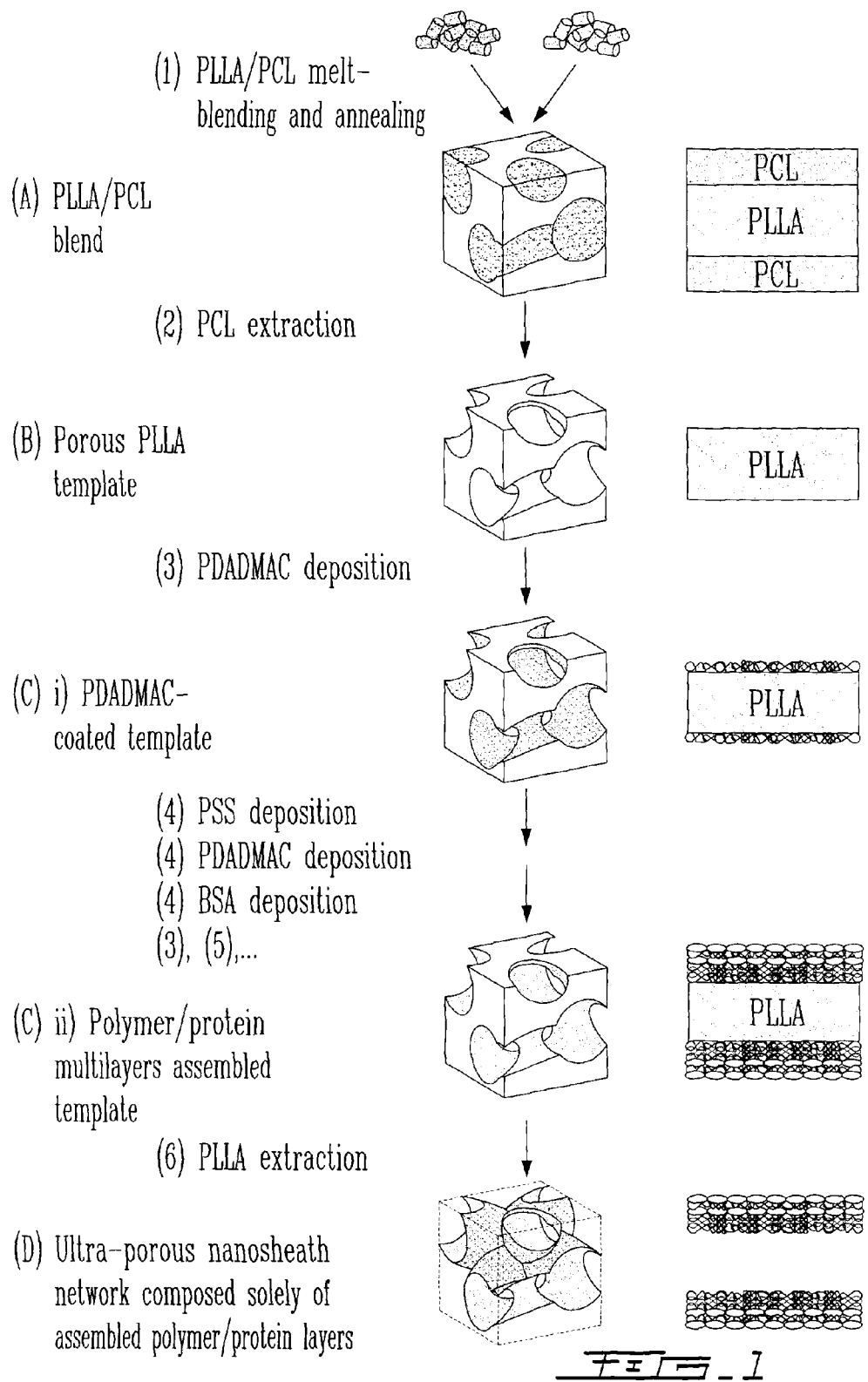
FIG. 1 is a schematic stepwise illustration of the method of the present invention for fabricating porous polymer/protein nanosheath networks.

Turning now to FIG. 1, the first step of the method is the blending of co-continuous synthetic polymer blends such as blends of poly(L-lactic acid) (PLLA) and poly(ε-caprolactone) (PCL), referred to as PLLA/PCL blends, via melt processing.

PLLA/PCL blends were prepared by melt-mixing in a Haake internal mixer at 200° C. and 50 rpm for 5 min. The blends were then quenched under liquid nitrogen to freeze-in the morphology. Depending on the protocol used, the annealing of the blends was carried out at the blend preparation temperature on a hot plate press without applied pressure for 2 hours.

Selective extraction of the PCL porogen phase in, for example acetic acid, yields a fully interconnected, highly continuous porous PLLA material.

The PLLA material was replicated (coated) by consecutively assembling polymer and protein by LBL deposition techniques onto the porous template.

More precisely, three precursor layers (PDADMAC/PSS/PDADMAC) were initially deposited to provide a uniformly charged surface and facilitate subsequent protein adsorption. The precursor film was formed by the alternate adsorption of PDADMAC [poly(diallyldimethylammonium chloride)] and PSS [poly(sodium 4-styrenesulfonate)] from aqueous solutions containing 10 mg ml$^{-1}$ of polyelectrolytes and 1 M NaCl. A vacuum/pressure cycle was used to force the penetration of the solution inside the hydrophobic PLLA templates. Polyelectrolytes were allowed to adsorb for 4 hours at room temperature. The samples were then washed for 4 hours in pure water under constant agitation. Using the same procedure, (BSA/PDADMAC)$_n$/BSA multilayers were deposited from 10 mg ml$^{-1}$ BSA [bovine serum albumin] solution in PBS (pH=7.0) (refs 20 and 21).

After deposition of the assembled molecular layers on the PLLA template, subsequent selective extraction of the PLLA leaves behind a network of nano-scale cylindrical sheaths.

These sheaths, composed solely of the self-assembled layers, when examined by electron microscopy, after a focused ion beam preparation approach (ref 19) were shown to possess a pore size similar to the original PLLA phase size, which was confirmed by BET measurements.

The typical sheath thickness is in the 100 nm range.

Precise pore sizes and narrow size distribution patterns may be achieved via controlling the pore size obtained by selective extraction of the co-continuous synthetic polymer blend. Indeed, it has been shown that pore sizes may be controlled over three orders of magnitude using quiescent annealing. (refs 7-10).

In order to demonstrate the preparation of materials of different pore sizes, two preparation protocols were used. The indication α refers to samples produced with the as-melt-blended material and β to samples obtained with material that was subject to quiescent annealing for 2 hours after the mixing stage. This latter operation caused an increase of the average size of the PCL continuous phase from 1.4 to 6.3 microns as determined from the internal surface area measurements using BET N$_2$ adsorption technique. Subsequent preparation of the porous substrate demonstrates that this pore size is maintained in the final material.

Still referring to FIG. 1, a detailed description of the method of preparation of the present invention now follows. The first stage is the preparation of co-continuous PLLA/PCL 50/50% wt. structures via melt blending. Gravimetric measurements show that the continuity of the PCL phase in the original PLLA/PCL blend is 96.2% for system α and 94.1% for system β. This clearly confirms the formation of co-continuous microstructures.

This co-continuous morphology is preserved during the subsequent annealing process for substrate β; only 2.1% of the continuity of the PCL phase is lost. The extraction of the PCL porogen phase yields a fully interconnected porous PLLA network of about 50% void volume. A small fraction of the PCL phase (3.8% and 5.9% of the weight of the initial PCL composition for Systems α and β respectively) remains imprisoned within the PLLA phase in the form of small segregated droplets. As anticipated, the internal surface area decreases in the case of the annealed structures β due to the increased phase size.

The uncharged fully continuous PLLA surface is then used as a template for the self assembly of PDADMAC and bovine serum albumin (BSA). The first PDADMAC layer adsorbs readily onto the hydrophobic PLLA surface and attaches at the interface via secondary and hydrophobic interactions (ref 22).

Figure 2:
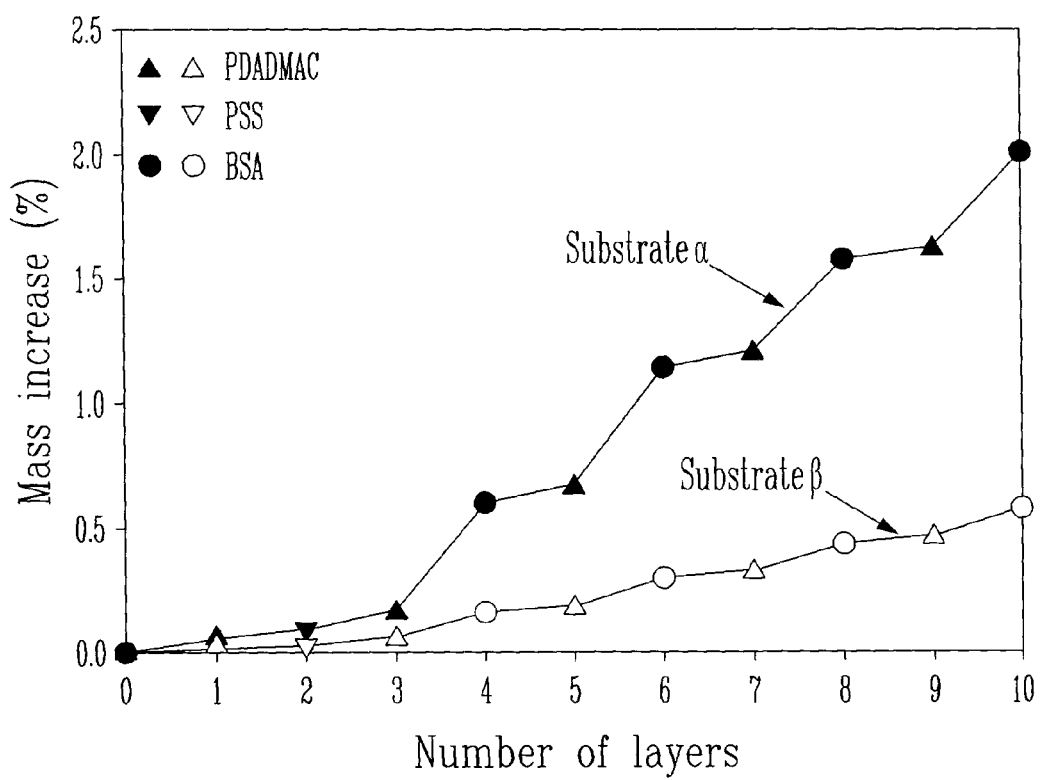
FIG. 2 shows the percentage of mass increase as a function of the number of PDADMAC/BSA layers assembled onto the internal surface of porous PLLA templates. (α; average pore size 1.4 μm and β; average pore size 6.3 μm)
Figure 4A:
FIG. 4 shows the properties of the structures produced at each stage of the preparation process and corresponding scanning electron micrographs of series β. Similar photomicrographs were obtained for series α.
Figure 4B:
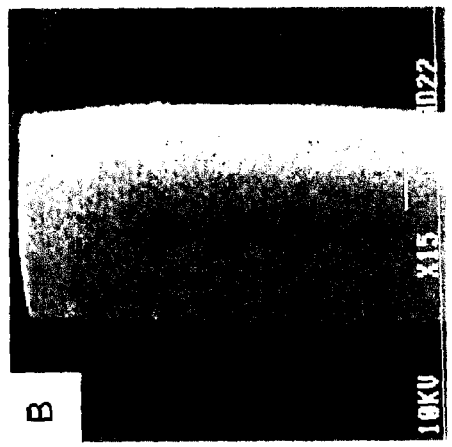
Figure 4C:
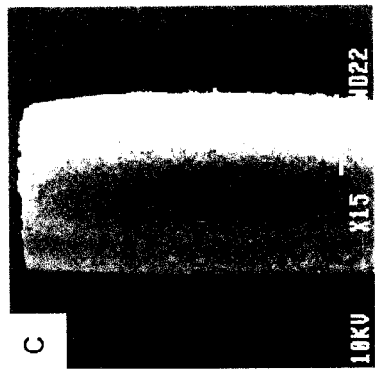
Figure 4D:
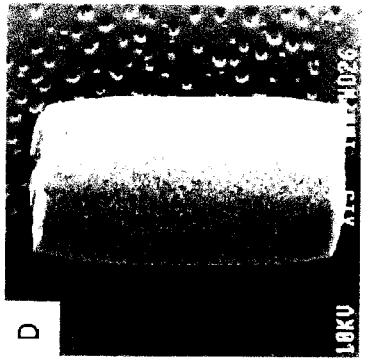

Turning now to FIG. 2, evidence for the PDADMAC/PSS/BSA 10 layer assembly is provided by gravimetric measurements. A constant mass of each species is deposited throughout the process; however, BSA adsorbs proportionally in greater quantity compared to the polyelectrolytes because of its globular conformation which allows for the formation of a more densely packed and thicker layer (refs 21 and 23). In all cases the amount adsorbed in a particular step is highly uniform. The variation between the two preparation protocols is, as mentioned earlier, the result of the annealing process which increases the phase size of β causing a decrease of the interfacial surface area and, therefore the adsorbed amount. Indeed, the ratio of the mass of BSA adsorbed onto the PDADMAC surface (α/β), $\eta_{mass}$=3.7, reasonably correlates with the ratio of the internal surface areas (α/β) $\eta_{surf}$=4.4.

The surface loading measurements for BSA on PDADMAC, $\theta_{BSA/PDADMAC}$, for both series α and β are as follows: ($\theta_{BSA/PDADMAC, \alpha}$=2.1 mg m$^{-2}$; $\theta_{BSA/PDADMAC, \beta}$=2.7 mg m$^2$).

The surface loading for BSA on PDADMAC surface was calculated by dividing the average amount of BSA adsorbed per deposition cycle (obtained from FIG. 2) by the internal surface area of the PLLA porous templates.

It was advantageously recognized that protein/polyelectrolyte multilayers fabricated by the LBL self-assembly technique possess a permeable structure (ref 24). Consequently, selective solvent extraction was possible through the self-assembled layers allowing access and solubilization of the PLLA template.

Throughout the extraction process of the PLLA template, solvent and solubilized PLLA molecules are thus able to permeate through the self-assembled film.

The extraction of samples β is advantageously performed in methylene chloride. Porous and partially transparent structures without deformation or cracking are obtained. Substrate a is best extracted in a mixture of methylene chloride/ethanol. Gravimetric measurements show that virtually no residual PLLA is left in samples β after extraction while in the case of samples α, 0.4% of the initial mass of PLLA is still present.

FIG. 3 demonstrates the morphology of both series through the preparation procedure. The effect of annealing (β) on the pore diameter after PCL extraction (Stage B) is illustrated in FIGS. 3A and 3B. After LBL deposition and extraction of the PLLA (FIGS. 3C and 3D), it can be seen that the pore size of the porous materials is similar to the phase size in the corresponding blend template. The microstructure generated is the replicate of the interface of the initial co-continuous polymer blend.

In some samples (α) the PLLA template was only partially extracted (FIG. 3E). To do so, an 8 hour extraction was performed instead of the usual 48 hours for a complete extraction.

Materials with significantly thicker walls, and hence better mechanical properties, are obtained by leaving a portion of the PLLA layer as an additional support of the final structure. This approach may also serve to control the void volume fraction of the network. A sheath longitudinal and cross section is clearly visible in FIG. 3E while FIG. 3F illustrates a typical nanosheath thickness of about 100 nm for substrate β. It is particularly clear on this figure that the nanosheaths are not fibrous. Indeed, it is clear on FIGS. 3D and 3F that the nanosheaths are not fibrous-like.

FIG. 4 shows the properties of the structures for α and β at each stage of the process. The overall shape and approximate dimensions of the samples are preserved at any point of the procedure. The radial marks observed on the outer skin of the substrates are artifacts generated by the knife during the initial shaping process but are not present in the internal morphology.

A flowsorb 2300 BET instrument was used to measure the surface area of the samples. Thereby, the number average diameter ($d_n$) is obtained from the volume/surface ratio ($d_n$=4V/S).

After stage B, the effect of annealing of the initial PLLA/PCL blend on the pore size can be seen. The phase growth observed during annealing decreases the interfacial surface area of the co-continuous blend and thus decreases the internal surface area available for deposition.

Still referring to FIG. 4, properties of the structures produced at each stage of the preparation process and corresponding scanning electron micrographs of series β are shown. Similar photomicrographs were obtained for series α.

Once the supporting PLLA template structure is removed, the assembled polyelectrolyte/protein layers take the form of very thin sheaths.

One of the main advantages of the method of the present invention is that deposition of self-assembled multilayers onto a PLLA template surface and subsequent extraction of that surface should yield a structure with twice the surface area per unit volume of the original porous blend. Considering experimental uncertainties, the ratio ξ, of the internal surface area per unit volume of the final structure (Stage D) to that at the preceding Stage C, indicates that this is indeed observed for both the α and β series ($\xi_\alpha$=2.1 and $\xi_\beta$=1.7).

Finally, after stage D, substrate α possesses a void fraction of 98.7%, an internal surface area per unit volume of 2.3 µm$^{-1}$ and a specific surface area of 140 m$^2$ g$^{-1}$ while the annealed substrate β yields a void fraction of 99.6%, an internal surface area of 0.63 µm$^{-1}$ and a specific surface area of 63 m$^2$ g$^{-1}$.

A sample preparation technique using a focused ion beam (FIB) apparatus (ref 19) was used to prepare the porous materials for electron microscopy. This approach minimizes macroscopic deformation or collapse of the structure.

In accordance with the method of the present invention interconnected nanosheath network of ultra-high void fraction, high internal surface areas and uniform pore size were produced.

Advantageously, the method of the present invention is very versatile and high levels of control can be exercised over void fraction, surface area and pore size.

For example, virtually any polymer pair can be used to prepare the original co-continuous blend template. This potentially allows one to prepare such porous structures with pore sizes ranging from 100 nm to hundreds of microns.

In addition to that, a wide range of polymers can be self-assembled onto the template opening the door to a variety of potential uses including biomedical, catalysis and conductive polymer applications.

REFERENCES

1. A. G. Mikos et al., *J. Biomed. Mat. Res.* 27,183 (1993).
2. A. G. Mikos et al., *Polymer* 35, 1068 (1994).
3. L. D. Harris, B. S. Kim, D. J. Mooney, *J. Biomed. Mat. Res.* 42, 396 (1998).
4. C. Schugens, V. Maquet, C. Grandfils, R. Jerome, P. Teyssie, *J. Biomed. Mat. Res.* 30, 449 (1996).
5. C. Schugens, V. Maquet, C. Grandfils, R. Jerome, P. Teyssie, *Polymer* 37, 1027(1996).
6. T. Segura et al., *Biomaterials* 26, 359 (2005).
7. P. Sarazin, X. Roy, B. D. Favis, *Biomaterials* 25, 5965 (2004).
8. P. Sarazin, B. D. Favis, *Biomacromolecules* 4, 1669 (2003).
9. Z. H. Yuan, B. D. Favis, *Biomaterials* 25, 2161 (2004).
10. Z. H. Yuan, B. D. Favis, *AIChE J.* 51, 271 (2005).
11. G. Decher, J. D. Hong, J. Schmitt, *Thin Solid Films* 210, 831 (1992).
12. G. Decher, *Science* 277, 1232 (1997).
13. S. T. Dubas, J. B. Schlenoff, *Macromolecules* 32, 8153 (1999).
14. J. B. Schlenoff, S. T. Dubas, *Macromolecules* 34, 592 (2001).
15. E. Popotshev, B. Schoeler, F. Caruso, *Langmuir* 20, 829 (2004).
16. B. Schoeler, G. Kumaraswamy, F. Caruso, *Macromolecules* 35, 889 (2002).
17. F. Caruso, R. A. Caruso, H. Möhwald, *Science* 282, 1111 (1998).
18. E. Donath, G. B. Sukhorukov, F. Caruso, S. A. Davis, H. Möhwald, *Angew. Chem. Int. Ed.* 37, 2201 (1998).
19. N. Virgilio, M.-F. Pépin, P. Desjardin, G. L'Espérance, B. D. Favis, *Macromolecules* 38, 2368 (2005).
20. Y. Lvov, K. Ariga, I. Ichinose, T. Kunitake, *J. Am. Chem. Soc.* 117, 6117 (1995).
21. F. Caruso, H. Möhwald, *J. Am. Chem. Soc.* 121, 6039 (1999).
22. N. A. Kotov, *Nanostructured Materials* 12, 789 (1999).
23. J. Kim, G. A. Somorjai, *J. Am. Chem. Soc.* 125, 3150 (2003).
24. F. Caruso, D. N. Furlong, K. Ariga, I. Ichinose, T. Kunitake, *Langmuir* 14, 4559 (1998).

What is claimed is:

1. A method for making a porous material, said method comprising the steps of:
   (a) melt-blending two or more non-miscible polymers to obtain a co-continuous melt;
   (b) solidifying the melt of step (a) to obtain a solid mass;
   (c) selectively extracting at least one of the polymers from said solid mass with a solvent, thereby creating an essentially continuous pore network within said solid mass, said pore network having an internal surface;
   (d) depositing one or more precursor layers on the internal surface of said pore network, wherein each of said one or more precursor layer is a polyelectrolyte layer;
   (e) replicating the internal surface of the pore network within said solid mass by coating said internal surface with successive material layers; and
   (f) selectively extracting said solid mass with a second solvent without extracting said layers, thereby producing a porous material.

2. The method of claim 1 wherein said material layers are polymeric layers.

3. The method of claim 2 wherein the last material layer contains functional chemical groups.

4. The method of claim 2 wherein at least some of said polymeric layers are conductive.

5. The method of claim 2 wherein said polymeric layers are conductive.

6. The method of claim 1 further comprising, after step (b), quiescent annealing of the solid mass obtained.

7. The method of claim 1 further comprising after step (f), exchanging the second solvent and freeze-drying the porous material.

8. The method of claim 1, wherein a first precursor layer comprises poly(diallyldimethylammonium chloride), a second precursor layer comprises poly(sodium 4-styrenesulfonate), and a third precursor layer comprises poly(diallyldimethylammonium chloride).

9. The method of claim 1 wherein in step (f), the extraction is partial so as to provide the porous material within a partially extracted solid mass.

10. The method of claim 1 wherein in step (f), the extraction is total.

11. The method of claim 1 wherein in step (e), one or more of the successive layers comprises poly(diallyldimethylammonium chloride).

12. The method of claim 1 wherein in step (e), one or more of the successive layers comprises proteins, cell growth promoters, functionalizing agents or mixture thereof.

13. The method of claim 1 wherein in step (e), about half of the successive layers comprises a mixture of bovine serum albumin and poly(diallyldimethylammonium chloride) and wherein about half of the successive layers comprises bovine serum albumin and are essentially free of poly(diallyldimethylammonium chloride).

14. The method of claim 1 wherein in step (a), the non-miscible polymers are poly(L-lactic acid) and poly(ε-caprolactone).

15. The method of claim 1 wherein step in (a) is performed at about 200° C.

16. The method of claim 1 wherein in step (e), half of the successive layers comprises a mixture of bovine serum albumin and poly(diallyldimethylammonium chloride) and wherein about half of the successive layers comprises bovine serum albumin and are essentially free of poly(diallyldimethylammonium chloride).

* * * * *